United States Patent
Tichauer et al.

(10) Patent No.: US 11,813,100 B2
(45) Date of Patent: Nov. 14, 2023

(54) METHODS FOR QUANTITATIVE AND ENHANCED-CONTRAST MOLECULAR MEDICAL IMAGING USING CROSS-MODALITY CORRECTION FOR DIFFERING TRACER KINETICS

(71) Applicant: The Trustees of Dartmouth College, Hanover, NH (US)

(72) Inventors: Kenneth M. Tichauer, Chicago, IL (US); Scott C. Davis, Woodville, NH (US); Brian William Pogue, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 1037 days.

(21) Appl. No.: 15/402,077

(22) Filed: Jan. 9, 2017

(65) Prior Publication Data

US 2017/0119330 A1    May 4, 2017

Related U.S. Application Data

(63) Continuation-in-part of application No. 15/044,097, filed on Feb. 15, 2016, now Pat. No. 11,510,600, and
(Continued)

(51) Int. Cl.
*A61B 6/00* (2006.01)
*A61B 5/055* (2006.01)
(Continued)

(52) U.S. Cl.
CPC .............. *A61B 6/481* (2013.01); *A61B 5/055* (2013.01); *A61B 6/032* (2013.01); *A61B 6/037* (2013.01);
(Continued)

(58) Field of Classification Search
CPC ....... A61B 6/032; A61B 6/037; A61B 6/4417; A61B 6/481; A61B 6/5235; A61B 5/055;
(Continued)

(56) References Cited

U.S. PATENT DOCUMENTS

| | | | |
|---|---|---|---|
| 2006/0118742 A1 | 6/2006 | Levenson et al. | |
| 2007/0165927 A1* | 7/2007 | Muradyan | G06K 9/40 382/128 |

(Continued)

FOREIGN PATENT DOCUMENTS

| | | | | |
|---|---|---|---|---|
| WO | WO-2009019535 A1 * | 2/2009 | | G06T 7/0016 |
| WO | WO 2013/122710 | 8/2013 | | |

OTHER PUBLICATIONS

International Search Report and Written Opinion dated Oct. 7, 2015, for International Application No. PCT/US15/39728 (11 pages).

(Continued)

*Primary Examiner* — Boniface Ngathi
(74) *Attorney, Agent, or Firm* — Cozen O'Connor (57) ABSTRACT

An apparatus and method for medical imaging uses a first and second contrast agent, the second agent targeted to a particular tissue type. First images are obtained using the first agent, and second images using the second agent using medical imaging systems. An image processing system is adapted to process the first and second medical images by fitting parameters of a pharmacokinetic model to the first medical images, identifying a nontargeted tissue type, scaling the fitted parameters to best match the nontargeted tissue in the second medical images, executing the pharmacokinetic model to prepare a correction image, and generating corrected medical images by subtracting the correction image from the second medical images.

11 Claims, 4 Drawing Sheets

Related U.S. Application Data a continuation-in-part of application No. 14/767,836, filed as application No. PCT/US2014/016291 on Feb. 13, 2014, application No. 15/402,077 is a continuation of application No. PCT/US2015/039728, filed on Jul. 9, 2015, now Pat. No. 11,564,639, said application No. 15/044,097 is a continuation of application No. PCT/US2014/051356, filed on Aug. 14, 2014, and a continuation-in-part of application No. 14/375,311, filed as application No. PCT/US2013/024400 on Feb. 1, 2013, now Pat. No. 9,456,200, said application No. 15/044,097 is a continuation-in-part of application No. 14/373,443, filed as application No. PCT/US2013/022266 on Jan. 18, 2013, now abandoned, said application No. 15/044,097 is a continuation-in-part of application No. 14/370,713, filed as application No. PCT/US2013/020352 on Jan. 4, 2013, now Pat. No. 9,336,592.

(60) Provisional application No. 62/022,413, filed on Jul. 9, 2014, provisional application No. 61/866,282, filed on Aug. 15, 2013, provisional application No. 61/764,506, filed on Feb. 13, 2013, provisional application No. 61/594,862, filed on Feb. 3, 2012, provisional application No. 61/588,708, filed on Jan. 20, 2012, provisional application No. 61/583,092, filed on Jan. 4, 2012.

(51) Int. Cl.
  *A61B 6/03* (2006.01)
  *G06T 5/50* (2006.01)

(52) U.S. Cl.
  CPC .......... *A61B 6/4417* (2013.01); *A61B 6/5235* (2013.01); *A61B 6/5247* (2013.01); *G06T 5/50* (2013.01); *G06T 2207/10081* (2013.01); *G06T 2207/10088* (2013.01); *G06T 2207/10104* (2013.01); *G06T 2207/10108* (2013.01); *G06T 2207/20224* (2013.01); *G06T 2207/30024* (2013.01)

(58) Field of Classification Search
  CPC ............. G06T 5/50; G06T 2207/10081; G06T 2207/10088; G06T 2207/10104; G06T 2207/10108; G06T 2207/20224; G06T 2207/30024
  See application file for complete search history.

(56) References Cited

U.S. PATENT DOCUMENTS

| | | | | |
|---|---|---|---|---|
| 2007/0299335 | A1* | 12/2007 | Declerck | A61B 6/507 600/420 |
| 2008/0230703 | A1* | 9/2008 | Kadrmas | A61B 6/037 250/363.03 |
| 2009/0028408 | A1* | 1/2009 | Spies | A61N 5/1031 382/131 |
| 2009/0326362 | A1 | 12/2009 | Carlse et al. | |
| 2010/0106013 | A1 | 4/2010 | Morishita | |
| 2010/0296714 | A1* | 11/2010 | Schmainda | G01R 33/5601 382/131 |
| 2011/0058722 | A1* | 3/2011 | Hu | G06T 11/006 382/131 |
| 2011/0275932 | A1 | 11/2011 | Leblond et al. | |
| 2011/0293143 | A1* | 12/2011 | Narayanan | G06T 7/33 382/103 |
| 2011/0293162 | A1* | 12/2011 | Pajeau | G06T 5/50 382/132 |
| 2012/0134464 | A1* | 5/2012 | Hoernig | A61B 6/481 378/22 |
| 2012/0314925 | A1* | 12/2012 | Peligrad | A61B 6/037 382/131 |
| 2013/0259805 | A1 | 10/2013 | Bacskai | |
| 2014/0039300 | A1* | 2/2014 | Gjesdal | G01R 33/5608 600/420 |
| 2014/0121511 | A1* | 5/2014 | Kadrmas | A61B 6/037 600/431 |

OTHER PUBLICATIONS

Tichauer et al. (Jan. 2013), "Dual-tracer background subtraction approach for fluroescent molecular tomography." Journal of Biomedical Optics, vol. 18(1), 016003.
Tichauer et al. (Apr. 2014), "Accounting for pharmacokinetic differences in dual-tracer receptor density imaging", Phys. Med. Biol. 59 (2014)2341-2351.
International Preliminary Report on Patentability dated Jan. 10, 2017, for International Application No. PCT/US15/39728 (9 pages).
Final Office Action for U.S. Appl. No. 14/767,836 dated Jun. 6, 2022, 15 pages.
Tichauer et al., Computed Tomography-guided Time-domain Diffuse Fluorescence Tomography in Small Animals for Localization of Cancer Biomarkers, *Journal of Visualized Experiments*, 65, e4050, Jul. 2012, 5 pages.
Non-Final Office Action for U.S. Appl. No. 14/767,836 dated Aug. 30, 2021, 22 pages.
Pogue et al., "Imaging targeted-agent binding in vivo with two probes", *Journal of Biomedical Optics*, 15(3), 030513, 2010.
Tichauer et al., "Improved tumor contrast achieved single time point dual-reporter fluorescence imaging", *Journal of Biomedical Optics*, 17(6), 066001, Jun. 2012.

\* cited by examiner

METHODS FOR QUANTITATIVE AND ENHANCED-CONTRAST MOLECULAR MEDICAL IMAGING USING CROSS-MODALITY CORRECTION FOR DIFFERING TRACER KINETICS

RELATED APPLICATIONS

The present application is a continuation of International Application No. PCT/US2015/039728, filed 9 Jul. 2015, which claims priority to U.S. provisional patent application 62/022,413 filed 9 Jul. 2014.

The present application is also a continuation-in-part of U.S. patent application Ser. No. 14/767,836, filed 13 Aug. 2015, which a 35 U.S.C. § 371 filing of International Application No. PCT/US14/16291 filed 13 Feb. 2014 which in turn claims priority to U.S. Provisional Application 61/764,506 filed 13 Feb. 2013.

The present application is also a continuation-in-part of U.S. patent application Ser. No. 15/044,097, filed 15 Feb. 2016, which is a continuation of International Patent Application No. PCT/US2014/051356 filed 14 Aug. 2014 which claims priority to U.S. Provisional Application No. 61/866,282 filed 15 Aug. 2013. U.S. patent application Ser. No. 15/044,097 is also a continuation-in-part of U.S. patent application Ser. No. 14/373,443 filed 21 Jul. 2014 which is a 35 U.S.C. § 371 filing of International Patent Application No. PCT/US2013/022266 filed 18 Jan. 2013, which claims priority to U.S. Provisional Application No. 61/588,708 filed 20 Jan. 2012. U.S. patent application Ser. No. 15/044,097 is also a continuation-in-part application of U.S. patent application Ser. No. 14/375,311, now U.S. Pat. No. 9,336,592, filed 29 Jul. 2014 which is a 35 U.S.C. § 371 filing of International Patent Application No. PCT/US2013/024400 filed 1 Feb. 2013 which claims priority to U.S. Provisional Application No. 61/594,862 filed 3 Feb. 2012 and U.S. Provisional Application No. 61/583,092, filed 4 Jan. 2012. U.S. patent application Ser. No. 15/044,097 is also a continuation-in-part of U.S. patent application Ser. No. 14/370,713, now U.S. Pat. No. 9,456,200, filed 3 Jul. 2014 which is a U.S. National Phase Application of International Application No. PCT/US2013/020352 filed 4 Jan. 2013 which claims priority to U.S. Provisional Application No. 61/583,092 filed 4 Jan. 2012.

The entire content of each of the above applications is incorporated herein by reference.

This application is also related to U.S. patent application Ser. No. 13/145,505, now U.S. Pat. No. 8,948,851, filed 20 Jul. 2011, which is a U.S. National Phase application of International Application No. PCT/US09/66839 filed 4 Dec. 2009, which claims priority to U.S. Provisional Application No. 61/145,900, filed 20 Jan. 2009.

GOVERNMENT INTEREST

This invention was made with government support under grant numbers P01 CA084201, R01 CA156177, U54 CA151662, and R01 CA109558 awarded by the National Institutes of Health and grant number W81XWH-09-1-0061 awarded by the Department of Defense. The government has certain rights in the invention.

BACKGROUND

Many medical imaging modalities require, or allow for, administration of a contrast agent or tracer to improve image quality. In some modalities, such as in nuclear medicine, a tracer agent must be administered to generate an image. Some contrast agents or tracers are targeted or selective agents, in that they concentrate in, or label, a particular tissue type to a greater degree than they concentrate in, or label, other tissues; targeted agents include fluorescent or radioactive-tracer labeled antibodies, antibodies labeled with radiopaque dyes, as well as other substances—such as radioactive iodine—that are selectively absorbed by particular tissues. Contrast agents, which may or may not be targeted, may also include gadolinium and gadolinium-tagged agents, and other paramagnetic contrast agents useful in MRI imaging, as well as microbubble-based agents suitable for ultrasound imaging.

Contrast agents are typically specific to a particular modality of imaging. For example, technetium 99 m-labeled agents provide significant contrast in tissue when the tissue viewed with a gamma-ray camera, while such agents are typically not visible in, or otherwise affecting, X-Ray based imaging like CT scans. Some targeted agents are taken up and released by tissues at rates that differ with tissue type. This can provide useful information. Similarly, some targeted tracers, such as aminolevulinic acid (ALA), are prodrugs that only become fluorescent after they have been metabolized in tissue; rates of tracer uptake and metabolism of prodrugs can provide useful information about tumor vascularization and metabolism.

In addition to the differences in absorption caused by targeting functional groups, the pharmaceutical kinetics, or rates of absorption and release of contrast agents and tracers from tissue, vary with factors including lipid and water content of tissue, charge distribution on agent molecules, agent molecule sizes, tissue perfusion rates, blood and plasma concentrations, and rates of agent metabolism or excretion.

Unfortunately, many targeted agents have significant background leakage or penetration (non-specific uptake) and/or do not clear from non-targeted tissues quickly. As a result, many targeted imaging agents produce poor contrast between targeted and non-target tissues.

Extending tracer administration-to-imaging time to allow unbound tracer to clear can help in some cases; however, implementing longer wait times (hours and days) is difficult in a clinical setting as multiple visits may be required, and can be counterproductive since signal strength may also be lost over time, making it more difficult to resolve an image. This is particularly challenging for positron emission tomography (PET) scanners, and gamma cameras, which observe radioactive decay of short-lived radiotracers to form an image. Nonspecific uptake also makes single-tracer imaging non-quantitative.

We have, in a parent application, disclosed administering targeted and nontargeted fluorescent tracers having different fluorescent characteristics to a subject, then obtaining images of each tracer separately. The separate images of each tracer are then scaled and differenced to provide a difference image highlighting selective absorption of the targeted tracer. This technique works well when a difference image is only desired at one particular time after administration of the tracers, or when the pharmacokinetics of targeted and nontargeted tracers are similar We call this Dual-tracer Receptor Concentration Imaging (DT-RCI). The method of the prior application, however, failed to account for differences in pharmacokinetics between tracers, and required that the tracers be imaged using the same imaging modality. In many cases, this is often difficult or impossible to achieve, especially with clinical imaging systems. Additionally, while some gamma cameras can distinguish multiple isotopic tracers based on energies of emitted gamma rays, it is not possible to distinguish different positron-emitting isotopes in a PET scanner because gamma rays emitted by positron-electron annihilation events that all have similar energy. Furthermore, optical techniques are severely limited by depth penetration issues and thus are generally not used for deep-tissue, volumetric clinical imaging.

SUMMARY

An apparatus and method for medical imaging uses a first and second contrast agent, the second agent targeted to a particular tissue type. First images are obtained using the first agent, and second images using the second agent using medical imaging systems. An image processing system is adapted to process the first and second medical images by fitting parameters of a pharmacokinetic model to the first medical images, scaling the fitted parameters to best match nontargeted tissue in the second medical images, executing the pharmacokinetic model to prepare a correction image, and generating corrected medical images by subtracting the correction image from the second medical images.

In another embodiment, a method of medical imaging includes administering first and second contrast agents; generating first medical images in a first imaging modality using the first contrast agent; generating second medical images using the second contrast agent; and processing the first and second medical images by fitting parameters of a pharmacokinetic model to the first medical images, scaling the fitted parameters to model the second agent, executing the pharmacokinetic model to prepare correction images, and generating corrected medical images by subtracting the correction images from the second medical images; wherein the second contrast agent is an agent configured for uptake by a targeted tissue type.

DETAILED DESCRIPTION OF THE EMBODIMENTS

The invention includes methods to account for image-confounding nonspecific uptake of targeted imaging agents in medical imaging. Nonspecific uptake in molecular imaging is perhaps the largest obstacle to what many have predicted will be a revolution in medical imaging (imaging of specific biomarkers). The invention uses a second, nonspecific imaging agent, which may be imaged with a second imaging modality, to correct for nonspecific uptake and thus enable recovery of truly biomarker-specific images.

Molecular imaging, defined as acquiring images of specific molecular biomarkers in tissue, is widely considered the next frontier in medical imaging. Potential uses span almost every area of medicine including imaging of cancer, neurodegenerative diseases, bone health, cardiac function, and others. A molecular imaging protocol generally involves administering to a patient an imaging contrast agent, known as a tracer, targeted to a biomarker of interest, waiting for the tracer to interact with or bind to the target and unbound tracer to be cleared from the vicinity by the body, and then using an imaging system sensitive to the administered agent to acquire images; the images provide a representation of the distribution of the biomarker of interest. These images thus reveal the activity of specific molecular processes in tissue, such as over-expression of receptors on cancer cells, which can be valuable in diagnosis and treatment planning.

Because of the enormous potential to impact clinical practice, preclinical research, and clinical trials of therapeutics, broad efforts in the research community have produced countless tracers targeted to many potential biomarkers; however, few of these agents ever make it to routine clinical use. This is partly due to the problem of nonspecific uptake—the portion of tracer that does not bind to the biomarker of interest and is not cleared by the body before imaging—that degrades image specificity and may hide biomarker features by impairing contrast. Tracer clearance rates depend on a complex interaction between tracer molecular weight (size), charge, kidney and/or liver function, etc.

We provide methods to account for nonspecific uptake in molecular imaging, facilitating the recovery of truly biomarker-specific images, even shortly after tracer administration. This is achieved by administering two tracers, one targeted to the biomarker of interest and the other a non-targeted counterpart, and comparing the behavior of both tracers to one another to recover target-specific images.

We initially demonstrated this concept using two fluorescent tracers in fluorescent optical imaging systems. These tracers differed in binding ability to specific biomarkers, in an embodiment one was nonspecific and the other specific to a particular biomarker. These tracers were chosen to have similar kinetics and thus images obtained from each tracer could be compared directly with one another, as by scaling and subtracting images or applying a dual tracer compartmental modeling for quantitative imaging, to extract information on specific binding. The tracers were also chosen such that both tracers could be imaged with the same imaging modality, such as with fluorescence imaging systems at differing wavelengths. However, optical modalities generally cannot image deep sub-surface tissue in humans, and most non-optical clinical imaging systems cannot distinguish two tracers in the same tissue at the same time. Furthermore, it can be difficult to match kinetics of tracers.

Figure 2:
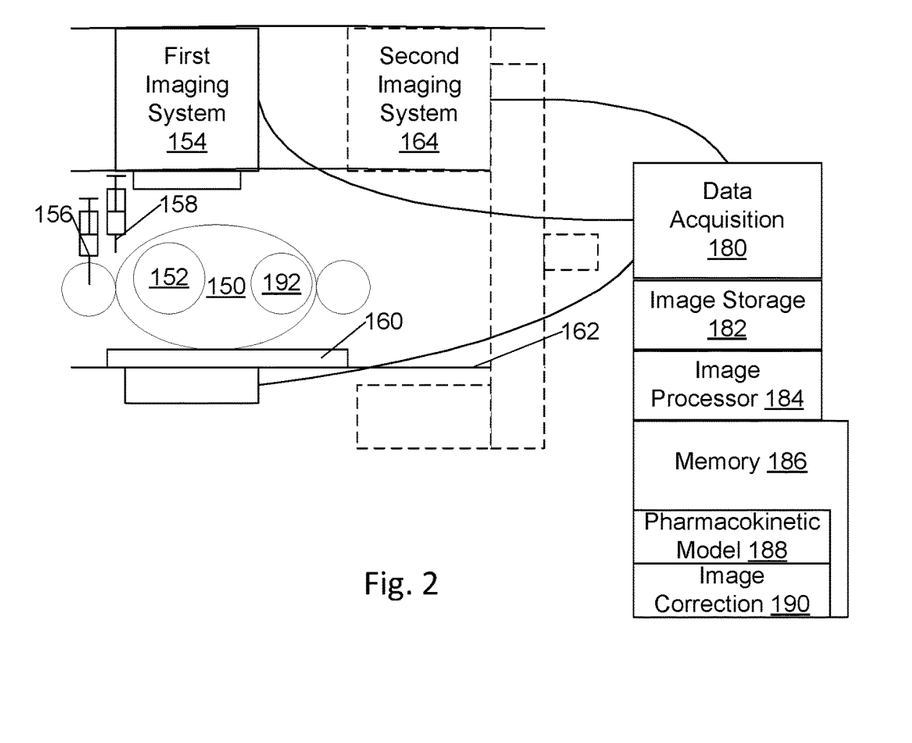
FIG. 2 is a block-diagram illustration of a generic imaging system for which the method of the present invention is applicable.
Figure 3:
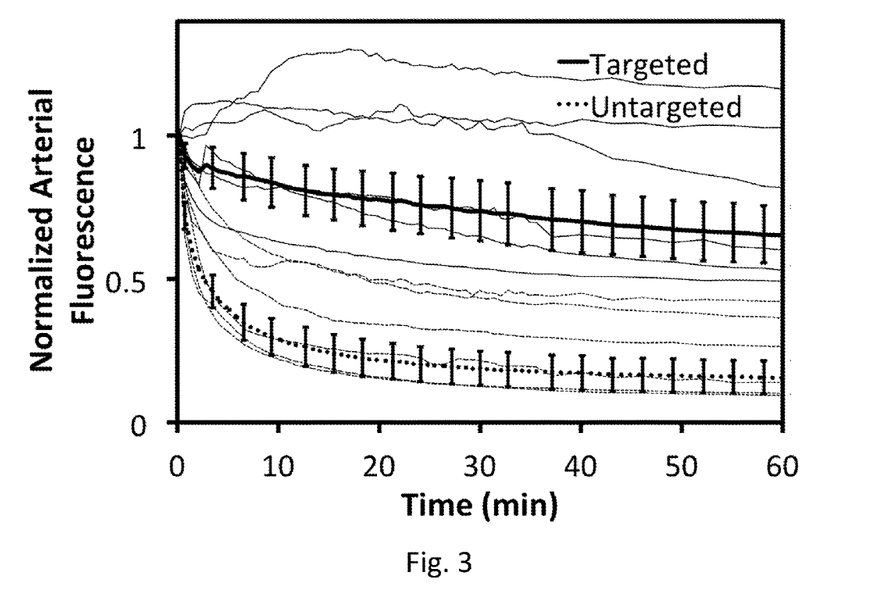
FIG. 3 Plots of the arterial input functions for EGFR-targeted and untargeted fluorescent affibodies measured from carotid artery fluorescence in 6 mice that were used in the simulations for targeted (blue data) and untargeted (red data) tracers Lighter lines represent the respective curves from the individual mice. Darker lines represent mean±standard deviation of the groups.
Figure 4:
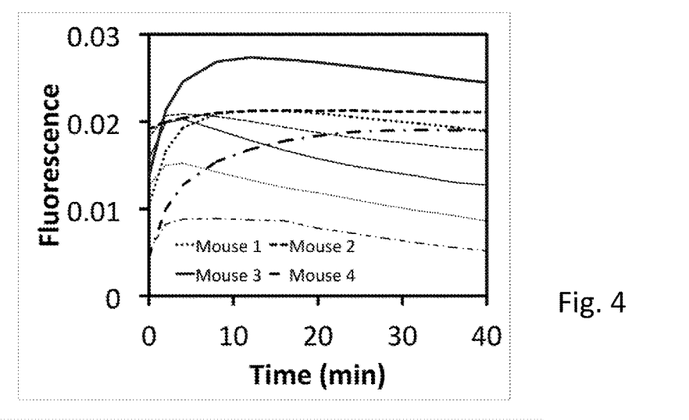
FIG. 4. Represents uptake curves of the targeted tracer (solid curves) and untargeted tracer (dashed curves) in leg muscle for four mice studied where line type represents results from a separate animal.
Figure 5:
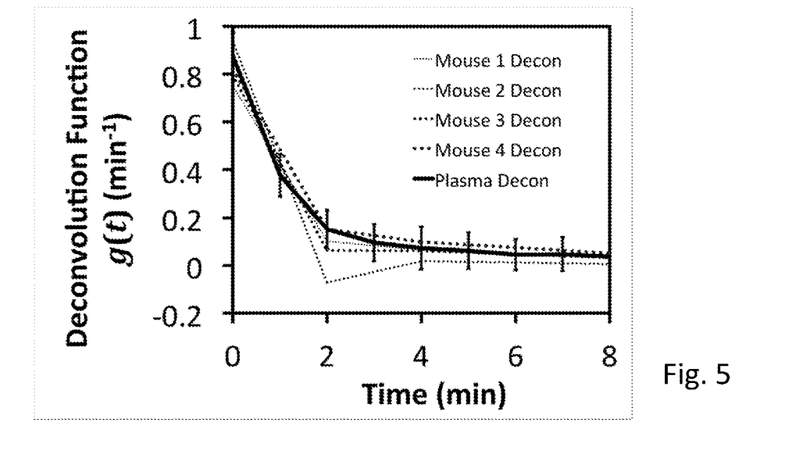
FIG. 5. Represents results of deconvolution of the targeted-untargeted tracer pairs displayed are presented with corresponding colors along with the deconvolution of the arterial input functions from FIG. 3 presented in solid black.
Figure 6:
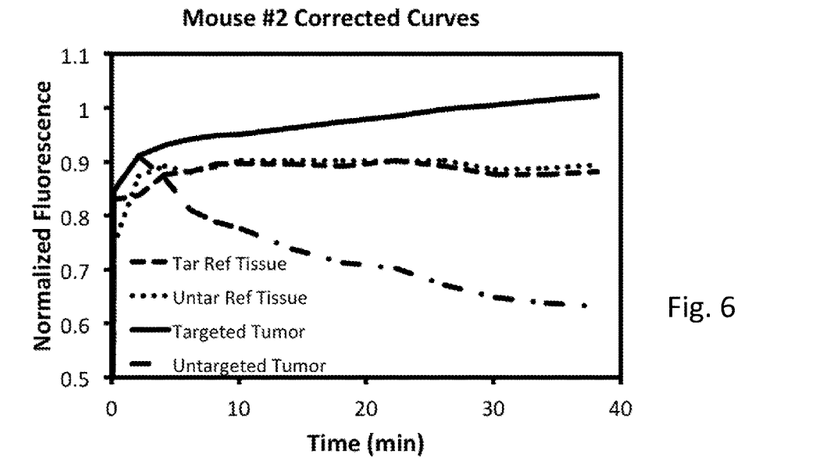
FIG. 6 illustrates typical "corrected" untargeted tracer uptake curves in the muscle ("Untargeted Ref Tissue"; dashed red curve) and tumor ("Untargeted Tumor"; solid red curve) of Mouse #2 are displayed alongside targeted tracer uptake curves in the muscle ("Tar Ref Tissue"; dashed blue curve) and tumor ("Targeted Tumor"; solid blue curve). The units of these curves are all normalized to the first measured data point.

We propose applying dual-tracer imaging using two or more tracers, operating on a system as illustrated in FIG. 2, selected from existing and future tracers, each imaged with a different imaging modality either simultaneously or nearly simultaneously. Some of these tracers are already approved for clinical use by relevant regulatory agencies, and others may be pending approval. For example, new MRI (Magnetic Resonance Imaging)-PET (Positron Emission Tomography) scanners can be used to image an MRI-sensitive contrast agent, in some embodiments as the non-targeted tracer, and a PET-sensitive contrast agent, in some embodiments as the targeted tracer. The method is equally applicable to embodiments using a PET-sensitive contrast agent as a non-targeted tracer and an MRI-sensitive contrast agent as a targeted tracer. Time-dependent image sets from both modalities, using first imaging system 154 (FIG. 2), and where imaging system 154 cannot image both tracers, using second imaging system 164. The image sets are acquired, either simultaneously, or nearly simultaneously through interleaved or sequential imaging, over time after administration of the two tracers and stored in image storage 182. Once the image sets are obtained, they are processed by image processor 184 as described below to highlight and resolve tissue targeted by the targeted tracer.

In embodiments, MRI-sensitive contrast agents or tracers may incorporate gadolinium into a molecule, and PET-sensitive contrast agents or tracers incorporate a positron-emitting radioactive isotope. In alternative embodiments, where patient movement between scans is minimized, the images are obtained on separate MRI and PET scan machines instead of on a dual-mode MRI-PET machine.

While PET is a modality adapted to image radioisotope concentrations at a first gamma energy equal to the energy of photons emitted by positron-electron annihilations, other imaging modalities for imaging radioisotope concentrations include gamma camera imaging, and single-photon emission computed tomography (SPECT). Gamma camera imaging and SPECT systems are typically adaptable to image photons of selected energies.

In an alternative embodiment, one tracer incorporates a non-positron-emitting radioisotope such as gamma-emitting Technetium 99-m (Tc-99m), or Iodine-123 or Iodine-131 (I-123 or I-131 respectively), this contrast agent is imaged either with a gamma camera or a SPECT (single-photon emission computed tomography) camera. Since tracers labeled with radioisotopes emitting gamma radiation at different energies can often be distinguished by pulse-height analysis in gamma cameras, and many gamma emitters like Tc 99-m, I-123 and I-131 can also be readily distinguished by gamma cameras and PET scanners using pulse height analysis from positron emitters, in an embodiment the second tracer may be selected from tracers labeled with a different gamma emitting radioisotope, or with a positron emitting radioisotope.

Similarly, in an alternative embodiment one tracer is a gamma-emitting radioisotope and the second tracer a tracer imageable in MRI scanners such as a gadolinium or magnetic nanoparticle-labeled tracer.

In yet another embodiment, a first tracer is a gadolinium-labeled or magnetic-nanoparticle tagged tracer imageable in MRI scanners and the second tracer is selected from a tracer labeled with a radioisotope and imageable with PET scanners, SPECT scanners, or gamma cameras, or an iodine-labeled tracers imageable in CT (X-ray computed tomography) scanners.

In yet another embodiment, the first tracer is a tracer having a short half-life in tissue and imageable in a first imaging modality, and the second tracer is also imageable in the first imaging modality. In this alternative embodiment, the first tracer is administered to a subject and a first sequence of images is obtained with the subject in a first position in the imaging system. After sufficient time for the first tracer to leave the subject, the subject is positioned as close as possible to the first position to ensure tissues of interest are in the same location in both the first and second image series, the second tracer is administered, and the second image series is obtained.

If the tracers have different uptake/clearance kinetics save for targeting, we use mathematical corrections to account for any differences in blood clearance rates between the tracers. Once corrected, the image series' for each tracer is processed to either enhance target contrast or quantify targeted tracer interaction with the target.

The processing methods involve two major steps, each of which can be accomplished using several techniques as described below:

Step 1. Correct for Differences in Non-Specific Kinetics Between Targeted and Untargeted Tracers to Prepare for Cross-Modality Image Processing by:

(a) Finding or developing (through chemistry) tracers with the same or very similar kinetics except for binding. If the two tracers have equivalent pharmacokinetics, no mathematical deconvolution is necessary to correct the uptake kinetics/arterial input functions of the tracers. A procedure to correct the images of the two tracers follows, including steps:

1) Register the images, or sequences of images, into a same coordinate system, as necessary.

2) Correct images, if necessary for one or both imaging modalities, for any background image present without tracer by subtracting pre-tracer images IT0 from post-tracer images IT1, IT2, or a post-tracer series of images, IT1($n$), IT2($n$), taken with both tracers T1 and T2 in one or two imaging modalities, and where n is a sequence number for images in each series: TempI1($n$)=IT1($n$)-IT0($n$); TempI2($n$)=IT2($n$)-IT0($n$), where T2 is the targeted tracer.

In an alternative embodiment, where background images are present without tracer, a correction of each with-tracer image is performed to enhance contrast by subtracting out a background pre-tracer image 3) Scale one or both image sequences to adjust for concentration differences between concentrations of the tracers, or the intensity with which each tracer is imaged in non-targeted tissues, e.g. TempI1$a$($n$)=a TempI1($n$), where a is a scalar determined for each image set.

These images are then analyzed using the techniques in Step 2, below.

(b) Applying a mathematical deconvolution process to determine a function which corrects for the differences in kinetic behavior between the two tracers. This can be accomplished using either arterial input functions to obtain the deconvolution function, and/or using tracer accumulation in a region devoid of the target to obtain a deconvolution function. The procedure to accomplish this with two tracers follows a similar procedure to what is described in Step 1(a), but including additional analysis as described below:

1) Register the images, or sequences of images, into a same coordinate system, as necessary.

2) Correct images, if necessary for one or both imaging modalities, for any background image present without tracer by subtracting pre-tracer images IT0 from post-tracer images IT1, IT2, or a post-tracer series of images, IT1(n), IT2(n), taken with both tracers T1 and T2 in one or two imaging modalities, and where n is a sequence number for images in each series: TempI1(n)=IT1(n)-IT0(n); TempI2(n)=IT2(n)-IT0(n), where T2 is the targeted tracer.

In an alternative embodiment, where background images are present without tracer, a correction of each with-tracer image is performed to enhance contrast by subtracting out a background pre-tracer image.

3) Scale one or both image sequences to adjust for concentration differences between concentrations of the tracers, or the intensity with which each tracer is imaged in non-targeted tissues, e.g. TempI1a(n)=a TempI1(n), where a is a scalar that may be determined for each image set.

Figure 1:
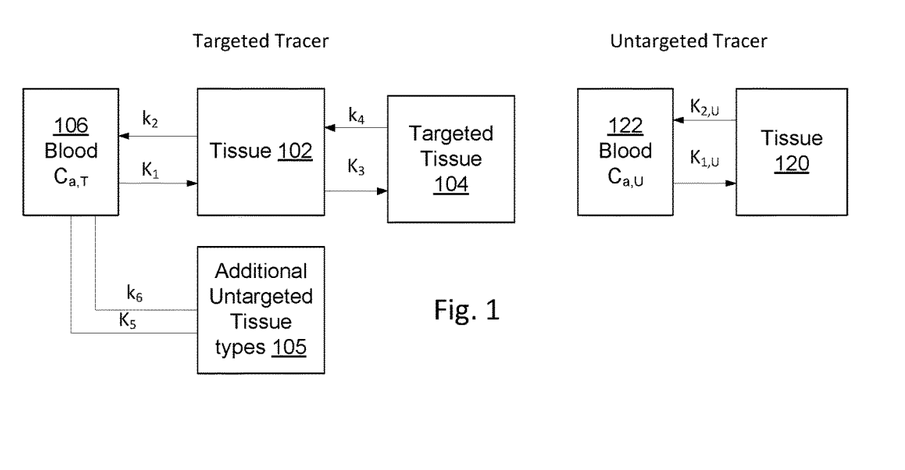
FIG. 1 is an illustration of rate constants K1, K2, K3, K4, K1U, K2U, for tracer flow between modeled pharmacologic reservoirs in the system.

4) Apply a deconvolution process: If we assume tracer kinetics follow a compartment model such as shown in FIG. 1, the arterial input function is represented as Ca(t). If the arterial input functions of a targeted tracer, $C_{a,T}(t)$, and untargeted tracer, $C_{a,U}(t)$, were to differ as a function of time, t, an expression can be derived to relate the two functions as follows:

$$C_{a,T}(t) = C_{a,U}(t) * g(t) \quad (1)$$

where * represents the convolution operator and g(t) is a function that converts $C_{a,U}(t)$ to $C_{a,T}(t)$. The function g(t) can be determined from Eq. (1) if the arterial input functions of the targeted and untargeted tracers were measured directly, either via a separate arterial concentration measurement system, or by segmenting arterial flow in the medical images to extract $C_{a,U}(t)$ and $C_{a,T}(t)$. A more flexible approach can be realized by comparing the uptake of the targeted tracer to the untargeted tracer in a tissue devoid of the target:

$$ROI\_no\_target_T(t) = ROI\_no\_target_U(t) * g(t)$$

In this target-free tissue, g(t) can be determined by deconvolving $ROI\_no\_target_T(t)$ by $ROI\_no\_target_U(t)$. Deconvolution is typically an unstable procedure, but one can adopt the approach developed by Diop and St. Lawrence which is based on general singular value decomposition and Tikhonov regularization (Diop M and St Lawrence K, 2012, *Deconvolution Method For Recovering The Photon Time-Of-Flight Distribution From Time-Resolved Measurements*, Optics letters 37 2358-60). Applying the deconvolution function, g(t), determined either from the arterial input function or from the ROI without targets corrects the image sets of both tracers to one another. These images are now ready for further analysis as described in Step 2.

Once a correction has been applied via one or a combination of the above steps, the targeted and untargeted tracer images may be compared directly to extract specific information about the target-to-targeted tracer activity. Assuming the kinetic correction is complete, the two image data sets are corrected to one another such that the only difference is target activity. A simple scaling/subtraction/ratioing method may be used to highlight biomarker activity contrast or kinetic modeling of the tracers for quantitative imaging of biomarker activity, as described in Step 2.

Step 2. Emphasize Target-Based Contrast and/or Quantify Target-To-Targeted Tracer Activity by:

(a) Apply a simple subtraction/ratio-ing/comparison of corrected images: If it is desired to emphasize the difference in target binding (increase target-specific contrast) without need for quantification of the target activity, a simple difference calculation at some timepoint or timepoints after the tracers have been administered may suffice. This can be achieved by subtracting, ratioing, scaling and subtracting, or otherwise comparing the non-targeted image set from the corresponding images of the targeted image sequence, e.g. Idif(n)=TempI2(n)-TempI1a(n) or Iratio(n)=(TempI2(n)-TempI1a(n))/TempI1a(n).

While the images of the resulting difference image sequence $I_{dif(n)}$ may be directly displayed, they may also be enhanced to provide anatomical references by, for example, giving the difference images $I_{dif(n)}$ a particular color and superimposing it on a background image, or other image that provides anatomical references, of a different color. E.g. $I_{display(n)} = RED * I_{dif(n)} + GREY * I_{T0(n)}$. In modalities where a tracer, such as untargeted tracer $T_1$, is required to show anatomical references (such as Gamma cameras), the background image may be derived from one particular image taken with the untargeted tracer. E.g. $I_{display(n)} = RED * I_{dif(n)} + GREY * I_{T1(1)}$.

OR (b) Apply kinetic modeling to time-dependent image stacks of untargeted and targeted tracers to recover quantitative images of target activity: If quantitative information about target activity/concentration is required, a full mathematical model described herein can be applied to the corrected images to calculate images of target-to-targeted tracer activity. For example, the uptake kinetics of the targeted tracer can be represented by a two-tissue compartment 102, 104, plus a blood compartment 106, model (FIG. 1), while those of the untargeted tracer (used to account for non-specific uptake of the targeted tracer) are represented by a one-tissue compartment 120 for each tissue type plus a blood compartment 122 model. With the targeted tracer (left), one 104 of the two tissue compartments represents targeted tissue, while another compartment 102 represents untargeted tissue of the same organ. Additional reservoirs 105 of untargeted tissues may exist in a patient imaged with targeted tissues having a different set of absorption and release parameters. A system of differential equations can be used to model the concentrations in targeted tissue, as follows in equation 1:

$$\frac{dC_{f,T}(t)}{dt} = K_1 C_{a,T}(t) - (k_2 + k_3) C_{f,T}(t) + k_4 C_{b,T}(t) \text{ and} \quad (2)$$

$$\frac{dC_{b,T}(t)}{dt} = k_3 C_{f,T}(t) - k_4 C_{b,T}(t),$$

where Ca,T, Cf,T, and Cb,T represent the concentrations of targeted tracer in the arterial plasma, in the extravascular space (unbound or "freely associated"), and in the extravascular space and bound to the targeted cell surface receptor, respectively; K1 and k2 are the rate constants governing transport of the targeted tracer between the blood and extravascular space; and k3 and k4 are rate constants governing association and dissociation of targeted tracer binding. A similar differential equation (Eq. 3) is used to represent the untargeted tracer one-compartment kinetic model:

$$\frac{dC_{f,U}(t)}{dt} = K_{1,U}C_{a,U}(t) - k_{2,U}C_{f,U}(t), \quad (3)$$

where $C_{a,U}$ and $C_{f,U}$ represent the concentrations of the untargeted tracer in the arterial plasma and freely associated in the extravascular space, respectively; and K1,U and k2,U are the rate constants governing transport of the untargeted tracer between the blood and extravascular space.

If the arterial input functions of the targeted and untargeted tracers are identical (as per Step 1(a) above), the differential equations in Eq. (2) and (3) can be solved to represent the measured uptake of the targeted tracer in any region of interest, ROIT, as a function of the measured uptake of the untargeted tracer in the same region of interest, ROIU, using the "simplified reference tracer model" approach as follows:

$$ROI_T(t) = R_1 ROI_U(t) + k_2\left[1 - \frac{R_1}{1+BP}\right]ROI_U(t) * e^{\frac{k_2}{1+BP}t}, \quad (4)$$

where $R_1 = K_1/K_{1,U}$, $BP = k_3/k_4$, and * represents the convolution operator. BP, the binding potential, is typically the salient parameter of interest as it is proportional to the concentration of targeted receptors available for tracer binding in a region of interest. Thus, spatial recovery of BP can provide quantitative images of specific biomarker activity, and this is achievable with tracers that have similar arterial input functions.

If, however, the arterial input functions of the targeted and untargeted tracers differ, their kinetics must be corrected to one another and equation (4) modified. Specifically, if the arterial input functions of a targeted tracer, $C_{a,T}(t)$, and untargeted tracer, $C_{a,U}(t)$, were to differ as a function of time, t, an expression can be derived to relate the two functions as follows:

$$C_{a,T}(t) = C_{a,U}(t) * g(t), \quad (5)$$

where g(t) is a function that converts $C_{a,U}(t)$ to $C_{aT}(t)$. By substituting Eq. (5) into the first expression in Eq. (2), Eq. (4) becomes:

$$ROI_T(t) = R_1 ROI_U(t) * g(t) + k_2\left[1 - \frac{R_1}{1+BP}\right]ROI_U(t) * g(t) * e^{\frac{k_2}{1+BP}t}. \quad (6)$$

Therefore, if g(t) were known, BP is estimated from Eq. (6) through non-linear fitting, even though the arterial input functions of the two tracers were different. g(t) can also be determined from Eq. (5) if the arterial input functions of the targeted and untargeted tracers were measured. A more flexible approach can be realized by comparing the uptake of the targeted tracer to the untargeted tracer in a tissue devoid of targeted binding (i.e., where a binding potential (BP)=0). With BP=0, and assuming $R_1 \cong 1$ (i.e., that $K_1 \cong K_{1,U}$), Eq. (6) simplifies as follows:

$$ROI\_no\_target_T(t) = ROI\_no\_target_U(t) * g(t) \text{ for } BP=0 \text{ and } K_1 = K_{1,U} \quad (7)$$

In this receptor-free tissue, g(t) can be determined by deconvolving ROI_no_target$_T$(t) by ROI_no_target$_U$(t) and then applied in Eq. (6). This technique allows BP to be recovered without the need for tracers with identical kinetic behavior.

Single Modality, Dual Tracer Imaging Using Deconvolution Correction.

We have shown that it is possible to correct for differences in the kinetic behavior of two tracers using a mathematical deconvolution technique. This was demonstrated for dual-tracer imaging in a single-modality (two optical tracers); however, the technique is extensible to cross-modality dual tracer imaging Ten female nude mice were inoculated subcutaneously on the right thigh, each with 10^5 cells of human U251 glioma line which is known to express a moderate level of epidermal growth factor receptor (EGFR). When the resulting tumors reached a diameter of 3 mm, the skin was removed from the tumors of four mice to measure tracer uptake in the tumor, and the carotids were exposed in the remaining 6 mice for a direct measure of the arterial input functions of the tracers. All mice were injected with an anti-EGFR (targeted) affibody molecule and a negative control (untargeted) affibody, which were labeled with the fluorophores, IRDye-800CW and IRDye-680RD (LI-COR Biosciences, Lincoln, Nebr.), respectively. A mixed solution containing 0.1 nanomoles of each tracer was injected into a tail vein of each mouse. In the four mice with exposed tumors, the uptake of these targeted and untargeted tracers was imaged in the tumor ("tissue of interest") and the leg muscle (devoid of EGFR; "receptor-free tissue") on a two-wavelength planar fluorescence imaging system at 1 min intervals for 40 min post-injection. In the six mice with exposed carotids, the arterial input functions of both tracers were imaged directly from the exposed vessels. Simulations demonstrated that blood, and to a lesser extent vascular-permeability, pharmacokinetic differences between targeted and untargeted tracers could be quantified by deconvolving the uptakes of the two tracers in a region of interest devoid of targeted tracer binding, and therefore corrected for, by convolving the uptake of the untargeted tracer in all regions of interest by the product of the deconvolution. Using fluorescently labeled, EGFR-targeted and untargeted Affibodies (known to have different blood clearance rates), the average tumor concentration of EGFR in four mice was estimated using dual-tracer kinetic modeling to be 3.9±2.4 nM compared to an expected concentration of 2.0±0.4 nM. However, with deconvolution correction a more equivalent EGFR concentration of 2.0±0.4 nM was measured.

Multi-Modality, Dual-Tracer Imaging

In concept, the approach described above for Single-Modality, Dual-tracer, Deconvolution Imaging can be applied to dual-modality, dual-tracer imaging In dual-modality imaging, a subject 150 (FIG. 2) having targeted tissue 152 is positioned 202 (FIG. 7) to be imaged by first imaging system 154. A first, targeted, tracer 156 is administered to the subject and a sequence of images of the first modality, the first modality being compatible with the first tracer 156, is obtained and digitized by data acquisition system 180 and stored 206 in an image memory 182. In some embodiments the imaging system 154 is reconfigured to obtain images in a second modality or, in some embodiments, the subject 150 is positioned on a table 160 configured to slide on rails 162 to reposition 210 subject 150 in a second imaging system 164 without disturbing soft tissues of subject 150 or allowing movement. A second, untargeted, tracer 158 is administered 212 and a sequence of images of the second modality, the second modality being compatible with the second tracer 158, is obtained and digitized by data acquisition system 180 and stored 214 in image memory 182. In some embodiments, including some embodiments where the imaging systems 164, 154 can readily distinguish between the tracers, the first and second tracer are mixed and injected simultaneously. In some embodiments, the first and second sequences of images are obtained simultaneously, in others the images alternate, and in others the first and second sequences are obtained sequentially without disturbing subject 150 between sequences to avoid shifting soft tissues of the subject.

The images in the image memory 182 are then processed by image processor 184. In embodiments where a significant difference in resolution exists between the first and second modality, edges are optionally extracted from the higher resolution modality and used in reconstruction of images of the lower resolution modality. Further, as has been done in existing PET-CT (Positron Emission Tomography —<X-Ray> Computed Tomography) systems, data from the higher-resolution modality may be used to correct images of the lower-resolution modality for other factors including attenuation by dense body parts.

Figure 7:
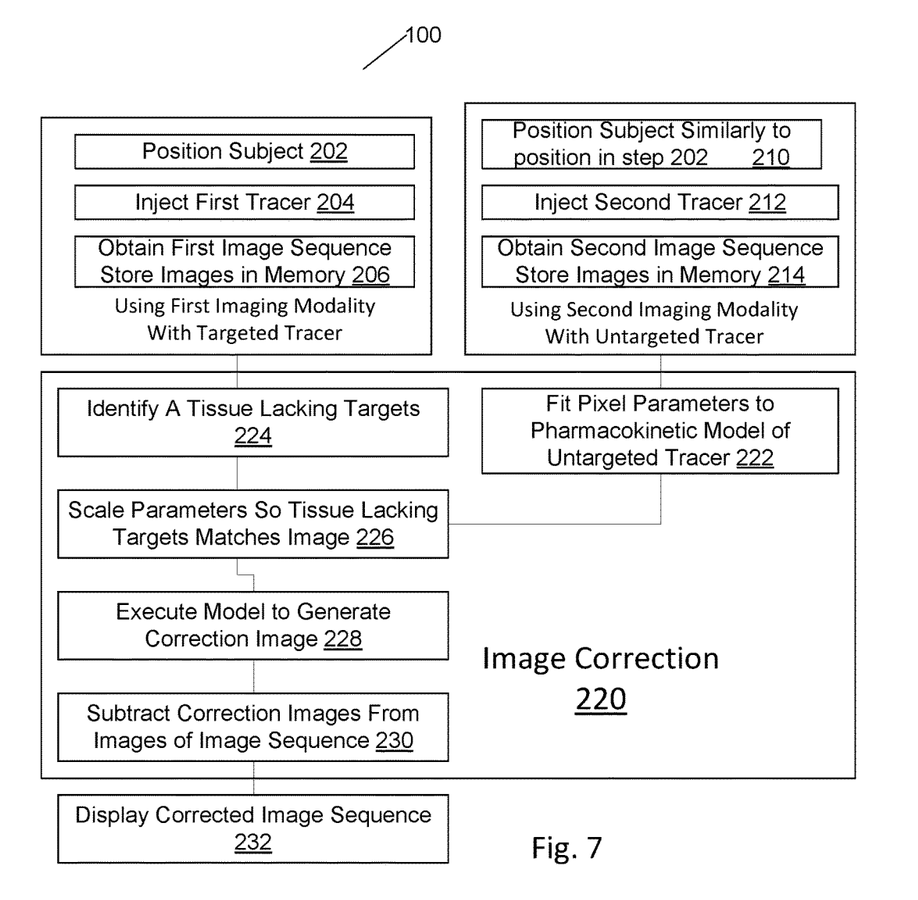
FIG. 7 is a dataflow diagram of the method of image correction.

The image processor 184 executes an image-correction 220 routine 190 from its program memory 186. The image-correction routine includes derivation 222 of pharmacokinetic model parameters for voxels or pixels of the second, untargeted, image sequence by fitting the model parameters to a pharmacokinetic model 188 of the second or untargeted tracer 158 on a per-pixel, or in an alternative embodiment a per-tissue, basis. Untargeted tissue 192, tissue that is expected to be devoid of molecular targets for the targeted tracer 156, in subject 150 is then identified 224. The derived pharmacokinetic model parameters are then scaled 226 by applying equation 6 as described above, such that subtraction of successive images of untargeted tissue 192 as refined by execution of the pharmacokinetic model 188 in an image sequence of the subject taken with the first modality with targeted tracer 156 present are close to null. Images of the first image sequence of the subject are then corrected by executing the pharmacokinetic model 188 to generate a correction image for each time and for each voxel, and subtracting 230 the correction image from the original images of the subject 150 taken with the first modality such that images of targeted tissue 152 are corrected for background first tracer 156. The resulting corrected image sequence is then displayed 232.

The method is believed applicable to hybrid CT(computed x-ray tomography)-PET (positron emission tomography) scanners, whereby a CT contrast agent is used as the untargeted reference to the PET's targeted tracer. However, CT generally has poor sensitivity to imaging agents, and imaging kinetics using multiple successive CT scans requires a fairly large radiation dose be imparted to the patient.

This approach could also be used with hybrid PET-gamma camera imaging, where two radioactive tracers, one being a positron emitter that results in emissions of 511 kev gamma-ray pairs, and the other being a gamma emitter with a significantly different energy, such as 140 kev $Tc^{99m}$. Pulse-height analysis can readily distinguish between gamma rays of these widely-separated energies, and coincidence analysis also permits distinguishing between positron-annihilation events and other gamma emissions.

A new generation of clinical hybrid systems has been introduced which couples PET and MRI. These scanners are suitable for applying this invention. Since the invention can be used with FDA-approved contrast agents (such as gadolinium DTPA for MRI and any PET tracer) it is possible to test the invention readily using clinical imaging data.

Therefore, the invention focuses on using multiple imaging modalities to image two tracers simultaneously, or nearly simultaneously, and correcting for the differences in tracer kinetics between the two modalities. Our device involves the process of acquiring tracer kinetics of both modalities and applying an algorithmic correction to extract target-specific images.

Since only a few points are necessary to fit parameters at each voxel to the pharmacokinetic model, the correction can be applied using only a few CT image acquisitions, this may help reduce patient radiation dosage while providing clinically useful images.

A new generation of hybrid clinical imaging systems which combine PET and MRI is gaining popularity. These systems are well-suited to take advantage of the invention. In this paradigm, MRI, which does not impart ionizing radiation, will be used to provide high resolution images of the non-targeted tracer dynamics, with the corresponding PET system providing co-registered images of targeted tracers.

In an alternative embodiment, three or more tracers, an untargeted tracer T1, and two or more targeted tracers T2, and T3, are administered, where targeted tracers T2 and T3 are targeted for different molecules in normal or abnormal tissues of the subject. Tracers T2 and T3 may, for example, be tracers each embodying an antibody, but with the antibodies targeted at different molecules. Images of tracer accumulation for all three tracers are obtained Images of both the first targeted tracer T2 and the second targeted tracer T3 are adjusted for tracer kinetics as heretofore described, first adjusted images $T2_{adjusted}$ of the first targeted tracer T2 using deconvolution using images obtained using untargeted tracer T1, then adjusted images $T3_{adjusted}$ of the second targeted tracer T3 are obtained using deconvolution using images obtained using untargeted tracer T1; both sets of adjusted images $T2_{adjusted}$ and $T3_{adjusted}$ are also adjusted for any background, pre-tracer (T0), images as necessary; each set being adjusted independently as heretofore described.

The adjusted images of each tracer $T2_{adjusted}$ and $T3_{adjusted}$ may then be further scaled and subtracted to provide additional information useful for diagnostic purposes. For example, but not limitation, first targeted tracer T2 may be targeted to a molecule found on normal tissue of a particular organ or tissue type, such as breast tissue or nerve tissue. Second targeted tracer T3 may be targeted to a molecule, such as an estrogen receptor for breast tissue, that is found in tumor tissue arising from the particular organ or tissue type with a concentration differing from a concentration of the same molecule in normal tissue of the same organ. Difference images between $T2_{adjusted}$ and $T3_{adjusted}$ may then prove useful in determining distribution of tumor within the normal tissue, or of determining distribution of a particular drug target within tumor tissue.

In a particular embodiment, each of the tracers, T1, T2, and T3, are independently imaged within the subject, are administered simultaneously, and are distinguished by different emissions energies, such as gamma ray energy from decay of radioactive tracers, or fluorescent emissions energies. In another particular embodiment, one or more tracer is imaged in a different imaging modality, for example but not limitation, T0 may be an X-ray dye imaged with a CT scanner, or a gadolinium-labeled molecule imaged with MRI, while T2 and T3 are differently-labeled radioisotopes. Similarly, in another sequential particular embodiment, one or more of the tracers is administered and imaged not simultaneously but in sequence with the other tracers to allow distinguishing between tracers in images.

The invention could be applied to any future hybrid imaging modalities suitable for multi-tracer imaging; as well as to current and future tracers such as those that may be based upon magnetic nanoparticles.

Combinations

The various features described herein can be combined in multiple ways. Among the combinations anticipated are those listed below:

An apparatus designated A for performing medical imaging including apparatus configured to administer a first contrast agent and a second contrast agent; a first imaging system operable in a first mode and configured to provide first medical images in a first imaging modality, wherein the first contrast agent is adapted to provide contrast in images of the first modality; imaging apparatus configured to provide second medical images, the imaging apparatus selected from the group consisting of the first imaging system operating in a second mode, and a second imaging system adapted to perform imaging in a second modality, wherein the second contrast agent is adapted to provide contrast in the second medical images while not providing significant contrast in the first medical images, and the first contrast agent is adapted to not provide significant contrast in the second medical images; and an image processing system adapted to process the first and second medical images by fitting parameters of a pharmacokinetic model to the first medical images, identifying a nontargeted tissue in the images, scaling the fitted parameters to best match the nontargeted tissue in the second medical images, executing the pharmacokinetic model to prepare a correction image, and generating corrected medical images by subtracting the correction image from the second medical images; wherein a contrast agent selected from the first and second contrast agent is an agent configured for uptake by a targeted tissue type.

An apparatus designated A1 including the apparatus designated A wherein generating corrected medical images is performed by subtracting the correction image from the second medical images.

An apparatus designated AA including the system designated A or wherein the imaging apparatus configured to provide second medical images is a second imaging system adapted to perform imaging in a second modality.

An apparatus designated AB including the system designated AA or A1 wherein the first modality is magnetic resonance imaging (MRI), and the second modality is a modality selected from the group consisting of X-ray computed tomography (CT), gamma camera imaging, positron emission tomography (PET), and single-photo emission computed tomography (SPECT).

An apparatus designated AC including the system designated AA wherein the first modality is X-ray computed tomography (CT) and the second modality is a modality selected from the group consisting of gamma camera imaging, positron emission tomography (PET), and single-photo emission computed tomography (SPECT).

An apparatus designated AD including the system designated AA wherein the first modality is a modality adapted to image radioisotope concentrations at a first gamma energy and selected from the group consisting of gamma camera imaging, positron emission tomography (PET), and single-photo emission computed tomography (SPECT).and the second modality is a modality adapted to image radioisotope concentrations at a second gamma energy selected from the group consisting of gamma camera imaging, and single-photo emission computed tomography (SPECT); where the first gamma energy differs from the second gamma energy.

An apparatus designated AE including the apparatus designated A wherein generating corrected medical images is performed by applying kinetic modeling to a plurality of images obtained at at least a first and a second time in the first imaging modality with the first contrast agent, and a plurality of images obtained at at least a third and a fourth time of the in the second imaging modality with the second contrast agent.

An apparatus designated AF including the apparatus designated AE wherein the kinetic modeling comprises a two-tissue compartment 102, 104, plus a blood compartment 106, model (FIG. 1) for each tissue type for the first tracer, and a one-tissue compartment 120 for each tissue type plus a blood compartment 122 model for the second tracer.

An apparatus designated AG including the apparatus designated AE or AF further including firmware in memory for applying a mathematical deconvolution process to determine a function which corrects for the differences in kinetic behavior between the first and second tracers. including additional steps: scaling an image sequence; and applying deconvolution.

A method of medical imaging designated B including: generating first medical images using a first medical imaging system using a first contrast agent in in a first imaging modality using the first contrast agent; generating second medical images using a second contrast agent; and processing the first and second medical images by fitting parameters of a pharmacokinetic model to the first medical images, scaling the fitted parameters to model the second agent, executing the pharmacokinetic model to prepare correction images, and generating corrected medical images by subtracting the correction images from the second medical images; wherein the second contrast agent is an agent configured for uptake by a targeted tissue type.

A method designated BA including the method designated B wherein the second medical images are obtained using a second imaging system adapted to perform imaging in a second modality different from the first imaging modality.

A method designated BB including the method designated B wherein the first modality is magnetic resonance imaging (MRI), and the second medical images are obtained using a second imaging modality selected from the group consisting of X-ray computed tomography (CT), gamma camera imaging, positron emission tomography (PET), and single-photo emission computed tomography (SPECT).

A method designated BC including the method designated B wherein the first modality is X-ray computed tomography (CT) and the second medical images are obtained using a second modality selected from the group consisting of gamma camera imaging, positron emission tomography (PET), and single-photo emission computed tomography (SPECT).

A method designated BC including the method designated B wherein the first modality is a modality adapted to image radioisotope concentrations at a first gamma energy and selected from the group consisting of gamma camera imaging, positron emission tomography (PET), and single-photo emission computed tomography (SPECT).and the second medical images are obtained using a second modality to image radioisotope concentrations at a second gamma energy selected from the group consisting of gamma camera imaging, and single-photo emission computed tomography (SPECT); where the first gamma energy differs from the second gamma energy.

An apparatus designated C configured for performing medical imaging including apparatus configured to administer a first contrast agent and a second contrast agent, the first and second contrast agent having similar pharmacokinetics; a first imaging system operable in a first mode and configured to provide first medical images in a first imaging modality, wherein the first contrast agent is adapted to provide contrast in images of the first modality; imaging apparatus configured to provide second medical images, the imaging apparatus selected from the group consisting of the first imaging system operating in a second mode, and a second imaging system adapted to perform imaging in a second modality, wherein the second contrast agent is adapted to provide contrast in the second medical images while not providing significant contrast in the first medical images, and the first contrast agent is adapted to not provide significant contrast in the second medical images; and an image processing system adapted with firmware in memory to process the first and second medical images by scaling the first medical images to produce a correction images matching a nontargeted tissue of the first medical images to the nontargeted tissue in the second medical images, and generating corrected medical images by subtracting the correction image from the second medical images; wherein a contrast agent selected from the first and second contrast agent is an agent configured for uptake by a targeted tissue type.

Apparatus designated CA including the apparatus designated C wherein the imaging apparatus is configured to provide second medical images is a second imaging system adapted to perform imaging in a second modality.

Apparatus designated CB including the apparatus designated C or CA wherein the first modality is magnetic resonance imaging (MRI), and the second modality is a modality selected from the group consisting of X-ray computed tomography (CT), gamma camera imaging, positron emission tomography (PET), and single-photo emission computed tomography (SPECT).

Apparatus designated CC including the apparatus designated C or CA wherein the first modality is X-ray computed tomography (CT) and the second modality is a modality selected from the group consisting of gamma camera imaging, positron emission tomography (PET), and single-photo emission computed tomography (SPECT).

An apparatus designated D for performing medical imaging including: apparatus configured to administer a first contrast agent and a second contrast agent, the first and second contrast agent having similar pharmacokinetics; a first imaging system operable in a first mode and configured to provide first medical images in a first imaging modality, wherein the first contrast agent is adapted to provide contrast in images of the first modality; imaging apparatus configured to provide second medical images, the imaging apparatus selected from the group consisting of the first imaging system operating in a second mode, and a second imaging system adapted to perform imaging in a second modality, wherein the second contrast agent is adapted to provide contrast in the second medical images while not providing significant contrast in the first medical images, and the first contrast agent is adapted to not provide significant contrast in the second medical images; and an image processing system adapted with firmware in memory to process the first and second medical images by fitting parameters of a pharmacokinetic model to images selected from the first and second medical images, using the pharmacokinetic model to process the first medical images into correction images, and generating corrected medical images from the correction images and second medical images; wherein a contrast agent selected from the first and second contrast agent is an agent configured for uptake by a targeted tissue type.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method of medical imaging comprising:
generating targeted medical images using a targeted contrast agent;
generating nontargeted medical images using a nontargeted contrast agent;
the targeted medical images being obtained using an imaging modality different from an imaging modality used to generate the nontargeted medical images;
the targeted contrast agent not providing significant contrast in the nontargeted medical images, and the nontargeted contrast agent not providing significant contrast in the targeted medical images; and
processing the nontargeted medical images and targeted medical images by fitting nontargeted parameters of a nontargeted pharmacokinetic model to the nontargeted medical images, deriving from the fitted nontargeted parameters a targeted pharmacokinetic model of the targeted contrast agent in tissue lacking a target of the targeted contrast agent, executing the targeted pharmacokinetic model of the targeted contrast agent to prepare correction images, normalizing the correction images to the targeted medical images, and generating corrected targeted medical images by subtracting the correction images from the targeted medical images;
wherein the targeted contrast agent is a targeted agent configured for uptake by a targeted tissue type; and
where the targeted agent is an agent that concentrates in tissue of interest to a greater degree than it concentrates in other tissues.

2. The method of claim 1 wherein a medical imaging system used to obtain the nontargeted medical images is adapted to perform imaging in a magnetic resonance imaging (MRI) modality, and a medical imaging system used to obtain the targeted medical images is adapted to perform imaging in an imaging modality selected from the group consisting of X-ray computed tomography (CT), gamma camera imaging, positron emission tomography (PET), and single-photo emission computed tomography (SPECT).

3. The method of claim 1 wherein a medical imaging system used to obtain the nontargeted medical images is adapted to perform imaging in an X-ray computed tomography (CT) modality, and a medical imaging system used to obtain the targeted medical images is adapted to perform imaging in an imaging modality selected from the group consisting of magnetic resonance imaging (MRI), gamma camera imaging, positron emission tomography (PET), and single-photo emission computed tomography (SPECT).

4. The method of claim 1 wherein a medical imaging system used to obtain the targeted medical images is adapted to perform imaging in a magnetic resonance imaging (MRI) modality, and a medical imaging system used to obtain the nontargeted medical images is adapted to perform imaging in an imaging modality selected from the group consisting of X-ray computed tomography (CT), gamma camera imaging, positron emission tomography (PET), and single-photo emission computed tomography (SPECT).

5. The method of claim 1 wherein a medical imaging system used to obtain the targeted medical images is adapted to perform imaging in an X-ray computed tomography (CT) modality, and a medical imaging system used to obtain the nontargeted medical images is adapted to perform imaging in an imaging modality selected from the group consisting of magnetic resonance imaging (MRI), gamma camera imaging, positron emission tomography (PET), and single-photo emission computed tomography (SPECT).

6. The method of claim 1 wherein the pharmacokinetic model is a two-compartment model.

7. The method of claim 1 wherein the pharmacokinetic model is a two-compartment model.

8. The method of claim 1 wherein the correction images are prepared by performing a mathematical deconvolution to determine a function which corrects for differences in between the nontargeted pharmacokinetic model and the targeted pharmacokinetic model of the targeted contrast agent and the nontargeted contrast agent.

9. The method of claim 1 wherein the nontargeted medical images have a first resolution and the targeted medical images have a second resolution different from the first resolution, wherein if the first resolution is greater than the second resolution the nontargeted medical images are used to sharpen edges of the targeted medical images, and wherein if the second resolution is greater than the first resolution the nontargeted medical images are used to sharpen edges of the targeted medical images.

10. The method of claim 1 where the targeted medical images are obtained at a first time and further comprising:
    generating targeted additional medical images using the targeted contrast agent at a second time, the second time different from a first time;
    re-executing the targeted pharmacokinetic model for the second time to prepare second correction images; and
    correcting the targeted additional medical images by subtracting the second prepared correction images from the targeted additional medical images.

11. The method of claim 1 where generating the correction images comprises identifying a nontargeted tissue type, and scaling the nontargeted medical images to best match the nontargeted tissue type in the targeted medical images.

* * * * *